(12) United States Patent
Chen

(10) Patent No.: US 9,643,028 B2
(45) Date of Patent: May 9, 2017

(54) RADIOTHERAPY APPARATUS

(75) Inventor: Rui Chen, Stockholm (SE)

(73) Assignee: ELEKTA AB (PUBL), Stockholm (SE)

( * ) Notice: Subject to any disclaimer, the term of this patent is extended or adjusted under 35 U.S.C. 154(b) by 127 days.

(21) Appl. No.: 14/396,989

(22) PCT Filed: Apr. 25, 2012

(86) PCT No.: PCT/EP2012/001767
§ 371 (c)(1),
(2), (4) Date: Jun. 25, 2015

(87) PCT Pub. No.: WO2013/159787
PCT Pub. Date: Oct. 31, 2013

(65) Prior Publication Data
US 2015/0352375 A1    Dec. 10, 2015

(51) Int. Cl.
*A61N 5/10*    (2006.01)
(52) U.S. Cl.
CPC .................. *A61N 5/1049* (2013.01)
(58) Field of Classification Search
CPC .......... A61N 2005/1061; A61N 5/1049; A61N 5/1067
See application file for complete search history.

(56) References Cited

U.S. PATENT DOCUMENTS

2007/0165779 A1    7/2007 Chen et al.

FOREIGN PATENT DOCUMENTS

WO    WO 04/000097 A2    12/2003

OTHER PUBLICATIONS

PCT International Search Report and Written Opinion from the European Patent Office, mailed on Sep. 20, 2012, in corresponding Application No. PCT/EP2012/001767 (9 pages).

*Primary Examiner* — Christine H Matthews
(74) *Attorney, Agent, or Firm* — Finnegan, Henderson, Farabow, Garrett & Dunner, LLP

(57) ABSTRACT

A radiotherapy apparatus includes a source of radiation, a patient support for locating a patient in the field of the source of radiation, a position detector for determining a position of a patient relative to the radiotherapy apparatus, a comparator for comparing the output of the position detector with a predetermined position, and a feedback system for informing the patient of the output of the comparator.

7 Claims, 3 Drawing Sheets

RADIOTHERAPY APPARATUS

CROSS REFERENCE TO RELATED APPLICATION

This is a U.S. National Phase of PCT/EP2012/001767, filed on Apr. 25, 2012. The entire content of this application is incorporated herein by reference.

FIELD OF THE INVENTION

The present invention relates to radiotherapy apparatus.

BACKGROUND ART

Radiotherapy is a method of treating tumours and like disorders by directing a beam of ionising radiation towards the tumour site. This radiation causes damage to tissues that it passes through, which inhibits and gradually reduces the tumour. It also causes damage to healthy tissue, albeit at a slightly lesser rate, so the beam is usually collimated to a cross-sectional shape that reflects the tumour shape; this may be the projected shape of the tumour along the current beam axis, or it may be some other shape designed to build up a specified dose distribution in the patient. In addition, the beam is also directed towards the patient from a number of different angles.

These measures for limiting the dose applied to healthy tissue and ensuring the adequate dose is applied to the tumour do depend on the patient being in a predictable location, and remaining there. Generally, prior to each treatment fraction a patient is positioned carefully by a clinician so as to place them in the correct position and orientation relative to the radiotherapy apparatus. The patient will also usually be supported on an adjustable couch that will allow fine-tuning of their position, preferably in all six degrees of freedom (three translational and three rotational), but sometimes fewer degrees of freedom such as the three translational degrees only, depending on the nature of the radiotherapy apparatus. Most radiotherapy apparatus also includes a means for monitoring the current patient position in real time, such as an IR based tracking system, a video camera, or the like.

Arrangements also exist for immobilising a patient; whilst these are often effective, they can be quite invasive and it may be desirable to avoid them where possible, depending on the circumstances of the patient.

Currently, if the monitoring systems detect that the patient has moved too much, the treatment is paused or aborted. This is undesirable in that it causes delay, but is better than continuing a treatment where the patient is misaligned.

SUMMARY OF THE INVENTION

Although patients are told to keep still during treatment, they receive no feedback as to their position during the treatment. This gives a feeling of uncertainty, and the position of the patient tends to drift by up to several millimeters over time. Also the accuracy of the immobilization is not as high as it might be as there is no way for the patient to correct his or her position during treatment.

We therefore propose a process of active position correction by the patient, based on movement feedback to the patient. To this end, we provide a radiotherapy apparatus comprising a source of radiation, a patient support for locating a patient in the field of the source of radiation, a position detector for determining a position of a patient relative to the radiotherapy apparatus (such as to a radiation focal point of the apparatus), a comparator for comparing the output of the position detector with a predetermined position, and a feedback system for informing the patient of the output of the comparator.

The feedback system can comprise a visual display, or an audible signal, or a haptic response, or any combination of these.

The feedback can be just the direction of the vector difference between the patient's current position and the predetermined position, or it can be a combination of the direction and the magnitude. Including the magnitude means that the patient can see how significant the misalignment is, but limiting the information to just the direction creates a simpler message that may be easier to act on.

There will still of course (usually) be a need for a control system arranged to monitor the output of the comparator and switch off the source of radiation if magnitude of the output of the comparator is greater than a preset threshold. The present invention then operates in the range of misalignments below that present threshold, helping the patient maintain a higher level of alignment and reducing the likelihood of the treatment having to be suspended.

BRIEF DESCRIPTION OF THE DRAWINGS

An embodiment of the present invention will now be described by way of example, with reference to the accompanying figures in which.

DETAILED DESCRIPTION OF THE EMBODIMENTS

The idea is to show the patient their movement during treatment. This enables the patient to see how he or she is moving and thus to compensate for those movements.

Figure 1:
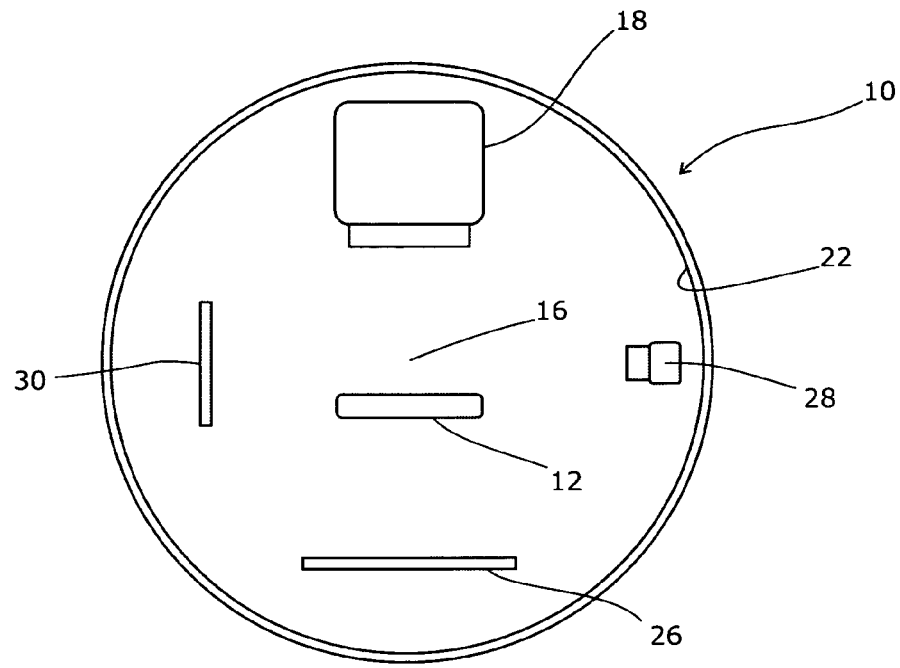
FIGS. 1 and 2 show a radiotherapy apparatus incorporating the present invention, from the front and from the side, respectively.
Figure 2:
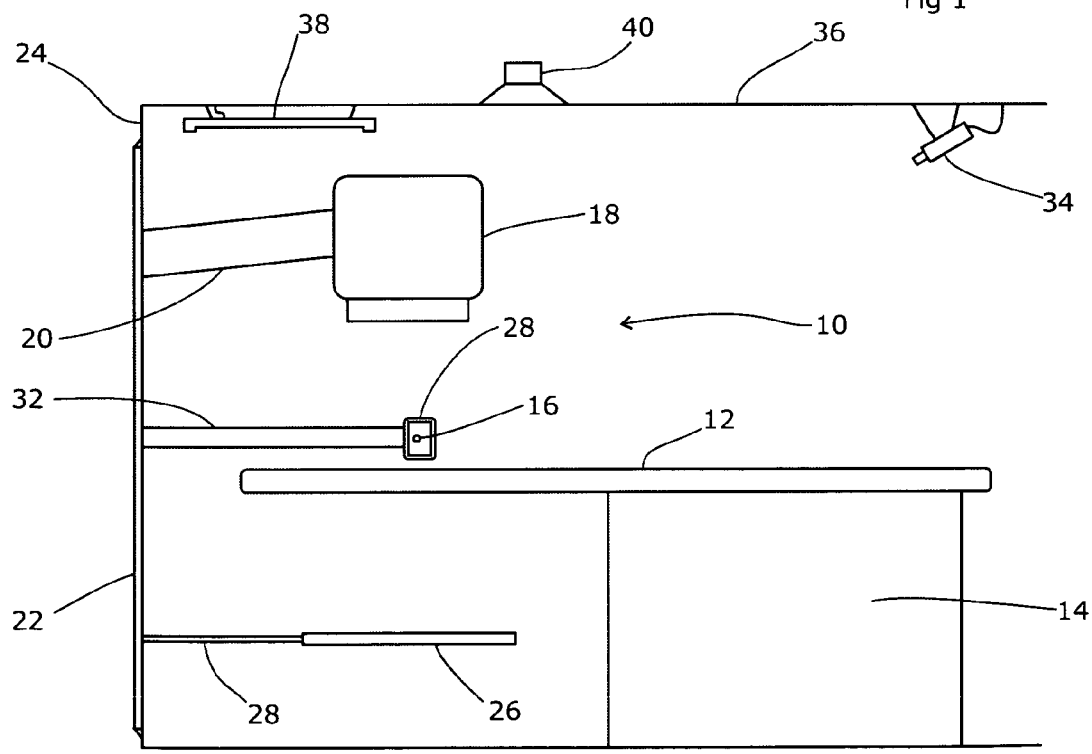

To this end, the radiotherapy apparatus 10 is provided as shown in FIGS. 1 and 2. A patient couch 12 is supported by a pedestal 14 so that a patient (not shown) can be positioned so that their tumour (or other region of interest) is substantially at, around or near an isocentre 16, i.e. a defined point in space within the room, that is often illuminated by alignment lasers. A radiation head 18 including a source of therapeutic radiation is mounted on a gantry 20 so that it emits a beam of either electrons or x-radiation with energy in the MeV range towards the isocentre 16. In this example, the source comprises a linear accelerator provided within the gantry and an x-ray target provided within the head 18 behind collimation systems including block collimators and a multi-leaf collimator.

Other types of radiotherapy apparatus exist, and the invention is equally applicable to these. For example, the Gamma Knife™ apparatus comprises a large number of individual isotopic radiation sources set in a substantial hemispherical collimator that collimates each source into a single beam aimed at a common isocentre at the centre of the hemisphere. This creates a high radiation intensity at the isocentre which drops rapidly away from that point. A patient can be positioned so that the tumour is located at the point, and a dose will then be applied to the tumour but not (significantly) to the surrounding tissue. This apparatus also requires the patient to maintain an accurate position, and hence the present invention is applicable in the same manner.

In the arrangement of FIG. 1, the gantry 20 and thus the source 18 are supported on a rotating carriage 22, of which only a front face is shown. In practice, the carriage 22 and the gantry 20 extend rearwards behind a wall 24 from which the gantry 20 appears to extend, to include a substantial rotating drum on which the gantry is fixed and which counterbalances the protruding part of the gantry 20 and the head 18.

This allows the head 18 to rotate around the patient; the axis of rotation is aligned with the isocentre 16 so that the centre of the beam emitted by the head always passes through the isocentre 16. This allows radiation to be directed toward the patient from multiple angles, thereby reducing the dose applied to healthy tissue.

A portal imaging panel 26 is supported on an arm 28 extending from the carriage 22, opposite the head 18. This detects the therapeutic x-ray beam after attenuation by the patient, and allows some analysis of the patient position and the treatment beam settings. The portal image suffers from a lack of detail, however, as the properties of the therapeutic beam do not lend themselves to good-contrast imaging. Accordingly, a second x-ray source is provided in the form of a diagnostic source 28 and an imaging panel 30, supported on arms 32 extending from the carriage 22 and spaced 90 degrees from the head 18. For clarity, the imaging panel 30 and its supporting arm are not shown in FIG. 2.

The apparatus is thus able to detect the patient position by analysis of the output of the imaging panel 26, and of the imaging panel 30. In addition, a video camera 34 is affixed to the ceiling 36 or other suitable mounting point, with a view of the isocentre 16 and the patient so that the patient position can be determined. A range of other patient tracking systems exist, including IR tracking systems such as NDI polaris, other optical systems such as the C-rad Catalyst, or ultrasound based systems such as the Resonant Clarity. Ultrasound systems can be incorporated into the patient support so as to scan the patient during the treatment process and detect movement. Generally, those systems relying on non-ionising radiation are to be preferred.

Feedback is provided for the patient in the form of a display panel 38 mounted on the ceiling 36 above the patient couch 12, and a loudspeaker 40. The display panel 38 is able to display visual feedback and the loudspeaker can provide audible feedback, as will be described below. A haptic feedback system can also be provided, as will be discussed. In practice, a single feedback system is likely to be enough and will prevent the patient becoming confused by a multiplicity of systems.

Figure 3:
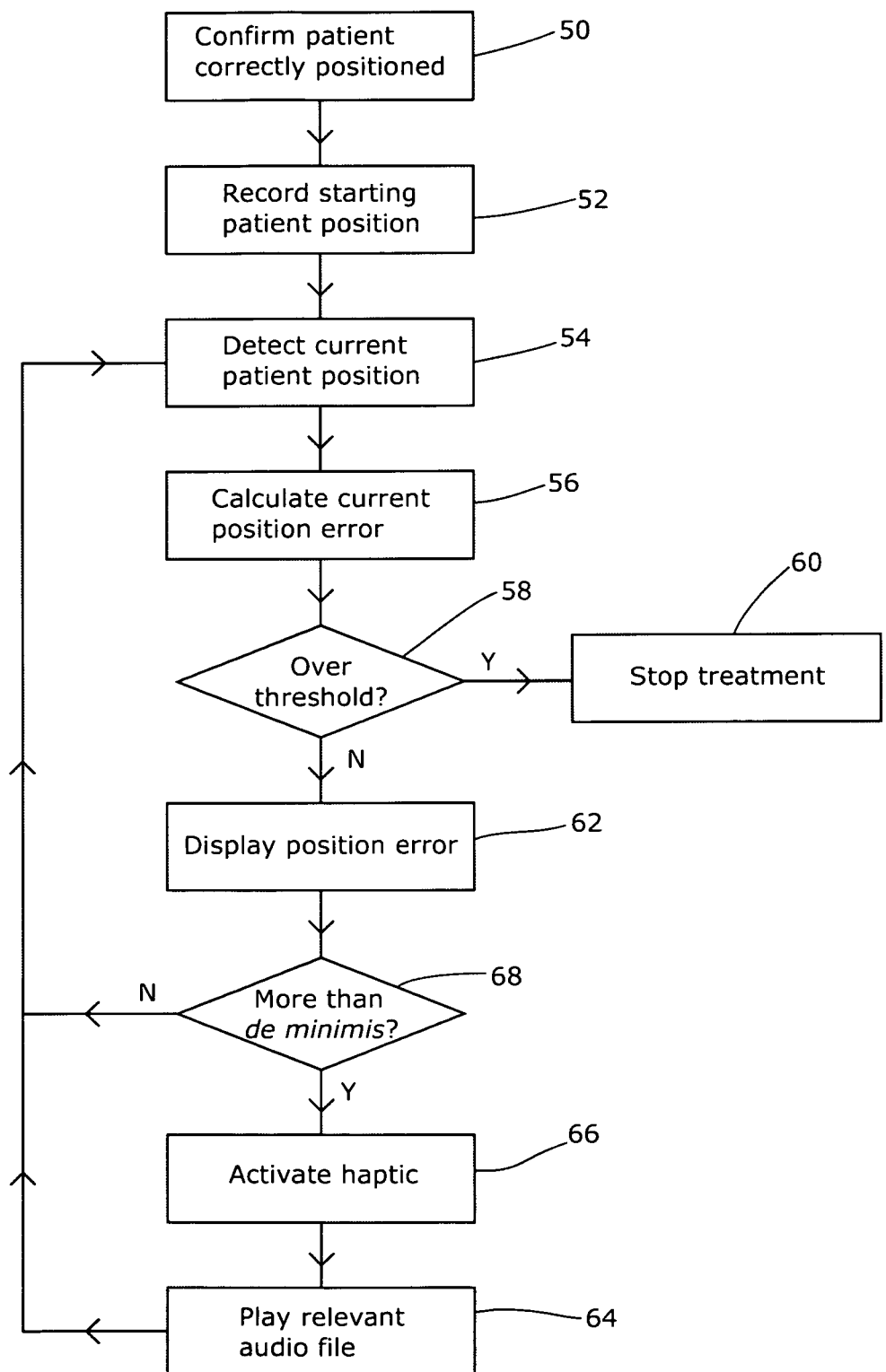
FIG. 3 shows a process diagram for the present invention.

An alternative to a display screen would be the use of video-glasses, such as those shown at http://www.vuzix.com/home/. A simpler alternative might be a light direction feedback system comprising at least four light sources such as LEDS are placed around the eye in or on a spectacle frame or the like (such as, eventually, a contact lens). If the patient is out of position, then the light sources can be illuminated in such a pattern that the patient is guided back to his original position by simply following the light. This is likely to work even if the eyes of the patient are closed, as enough light is transmissible through eyelids for the patient to be aware of where to look. FIG. 3 shows the process route to be adopted.

Once the patient is in position on the patient couch 12, the clinician can initialise the system and, in doing so, confirm that the patient is correctly positioned (step 50). This starting position of the patient is then detected using whatever patient tracking system is to be relied on (as above), step 52. The system can then enter the operating loop in which the patient's current position is detected (step 54) and compared to the starting position to yield a current position error (step 56) which is the vector difference between the two positions. The magnitude of that vector is then calculated and compared to a preset threshold (step 58); if over the threshold then the patient is considered to be out of range and the treatment is stopped (step 60).

If the current position error is less than the threshold, then the treatment can continue. However, there may be a small position error which, if left uncorrected, could be added to leading to a treatment-ending error. If the patient is alerted to this error, many will be able to try and correct it; this will both minimise the positional error and also reduce the likelihood of the treatment having to be ended prematurely so that the patient can be repositioned.

Therefore, the current positional error is displayed to the patient via the display 38 (step 62). It is also communicated to the patient via the audible feedback system 40 (step 64) and the haptic system (step 66). To prevent continual noise or interference with the patient, a check is first made that the positional error is more than a de minimis level (step 68) before providing audio or haptic feedback.

The system then re-checks the current patient position, step 54, starting the process once again. In this way, the patient can be kept up to date with their position as compared to their initial position, and can actively correct this towards that assumed-ideal initial position.

Naturally, if any of the feedback systems (visual, audible, and haptic) are not provided then the relevant step is omitted, and if any additional feedback systems are provided then these are activated at the relevant point in the process.

Figure 4:
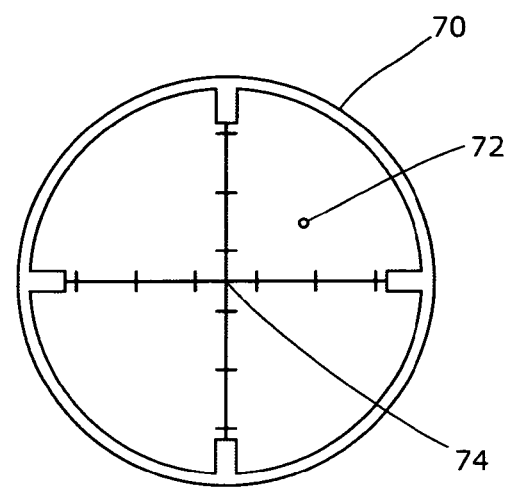
FIG. 4 shows a visual display for use in certain examples of the present invention.
Figure 5:
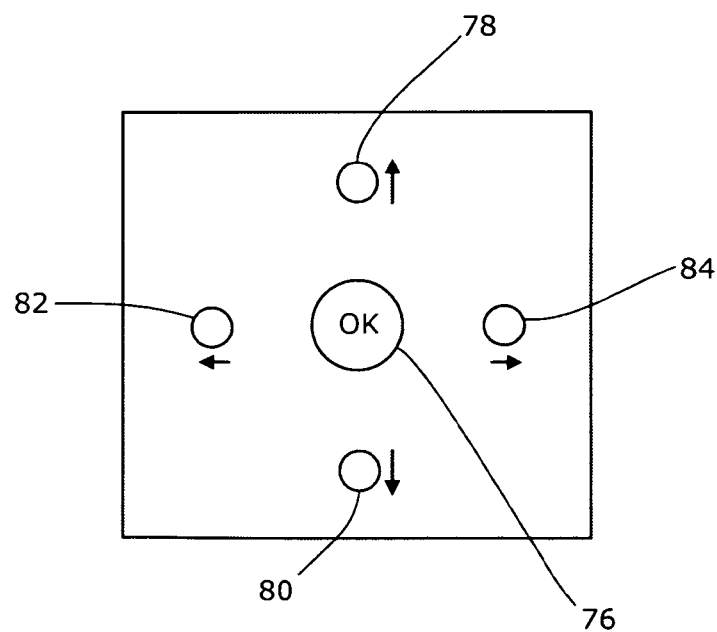
FIG. 5 shows an alternative visual display for use in certain examples of the present invention.

The largest patient movements are generally done along two axes, i.e. those in translation parallel with the couch 12 (or whatever device that the patient is lying on), and therefore it is sufficient to visualize the patients movements in two dimensions. When displayed via the panel 38, this can be done using a "crosshair" plot 70 (FIG. 4) where the patient's position is shown as a red point 72 that starts at the centre 74 and moves if the patient moves. It could also be simplified to just a few indicators (FIG. 6) showing the general direction to move in, consisting of just a central "OK" light 76 indicating an accurate placement, plus a pair of "up" and "down" lights 78, 80 and "left" and "right" lights 84.

The patient does not necessarily have to see the crosshairs 70, as the information can be given to the patient using other sensens and systems, such as a haptic feedback system or audio feedback. This system can be used in LINACS where patient movements usually are larger and therefore easier to compensate for if the patient is made aware of her movements, and in other forms of radiotherapy apparatus.

Figure 6:
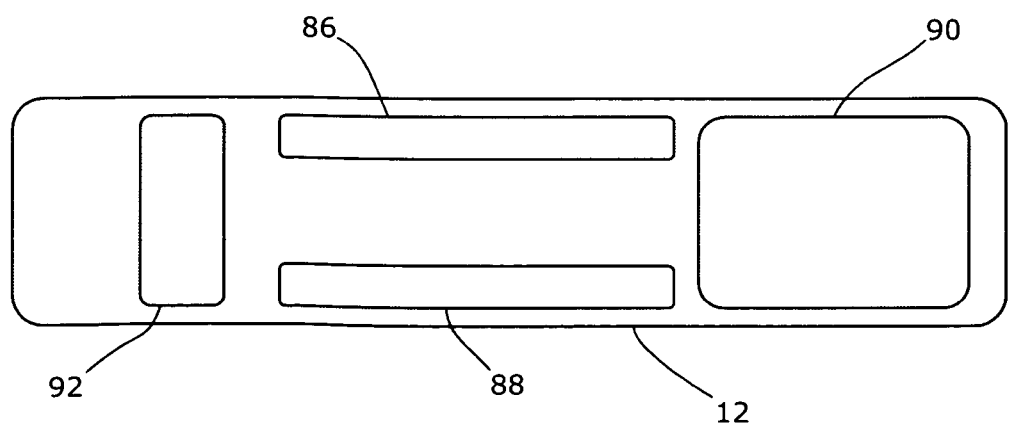
FIG. 6 shows a plan view of a patient support for use in certain examples of the present invention.

FIG. 6 shows some detail of a possible haptic feedback system. The patient couch 12 is provided with four gently-vibratable panels. These are a pair of side panels 86, 88 along the middle part of each side, a foot panel 90 at the end of the couch 12 on which the patient's lower legs and feet will rest, and a head panel 92 toward the end of the couch 12 on which the patient's head and shoulders will rest. This allows directional information to be communicated to the patient in a basic "up/down" and "left/right" pattern by activating the appropriate panel.

This is less likely to be suitable for use where the region of interest within the patient lies in an area that will be stimulated by the haptic panels 86, 88, 90, 92, as it will be undesirable to vibrate an area whose position is to be kept stable. However, it may be possible to impose a sufficiently gentle vibration that is detectable by the patient but not effective beyond the skin layer.

An alternative, and preferable haptic feedback system consists of four vibrators placed on the face of the patient, one on the forehead, one on the chin and one on each cheek. The appropriate vibrator is activated according to the direction that the patient needs to move their head. This works well for positioning the head, and can also be placed on other places such as on the arms, the legs, the body etc. Audible feedback can be provided by imply playing appropriate pre-recorded audio files via the loudspeaker 40, giving instructions such as "up", "down", "left", and "right" perhaps together with a magnitude indication such as "slightly", "a little" for small errors in order to avoid a feedback-induced oscillation of the patient. Audible feedback can also simply be a beep indicating that the patient needs to move. The patient can then look where to move on a display. This will enable the patient to close her eyes during treatment and not have to stare on a screen during the entire treatment.

Some older patients may not be used to using this kind of feedback systems, in those cases this system can be turned off and a more conventional immobilization can be used. The addition of this immobilization system to a treatment system will not hinder the operation of a conventional immobilization system. If audio or haptic feedback is used this system could even be used in combination with other immobilization systems such as immobilization based on a thermoplastic mask.

It will of course be understood that many variations may be made to the above-described embodiment without departing from the scope of the present invention.

The invention claimed is:

1. A radiotherapy apparatus, comprising:
a source of radiation;
a patient support for locating a patient in a field of the source of radiation;
a position detector configured to determine a position of the patient relative to the radiotherapy apparatus;
a comparator configured to compare an output of the position detector with a predetermined position; and
a feedback system configured to inform the patient of an output of the comparator,
wherein the output of the comparator includes a vector difference between the output of the position detector and the predetermined position, and the feedback system is configured to alert the patient as to a direction of the vector difference.

2. The radiotherapy apparatus according to claim 1, wherein the feedback system comprises a visual display.

3. The radiotherapy apparatus according to claim 1, wherein the feedback system comprises an audible signal.

4. The radiotherapy apparatus according to claim 1, wherein the feedback system comprises a haptic response.

5. The radiotherapy apparatus according to claim 1, wherein the position detector is configured to determine the position of the patient relative to a radiation focal point of the radiotherapy apparatus.

6. The radiotherapy apparatus according to claim 1, wherein the feedback system is configured to alert the patient as to both the direction and a magnitude of the vector difference.

7. The radiotherapy apparatus according to claim 1, further comprising a control system configured to monitor the output of the comparator and switch off the source of radiation when a magnitude of the output of the comparator is greater than a preset threshold.

* * * * *